(12) United States Patent  
Teucher et al.

(10) Patent No.: US 9,180,250 B2  
(45) Date of Patent: Nov. 10, 2015

(54) DRUG DELIVERY DEVICE

(75) Inventors: Axel Teucher, Frankfurt am Main (DE); Michael Jugl, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 407 days.

(21) Appl. No.: 13/503,293

(22) PCT Filed: Oct. 28, 2010

(86) PCT No.: PCT/EP2010/066313  
§ 371 (c)(1),  
(2), (4) Date: Sep. 12, 2012

(87) PCT Pub. No.: WO2011/051366  
PCT Pub. Date: May 5, 2011

(65) Prior Publication Data  
US 2013/0006192 A1    Jan. 3, 2013

(30) Foreign Application Priority Data

Oct. 30, 2009    (EP) .................................... 09174670

(51) Int. Cl.  
*A61M 5/24* (2006.01)  
*A61M 5/315* (2006.01)  
*A61M 5/31* (2006.01)

(52) U.S. Cl.  
CPC ............. *A61M 5/24* (2013.01); *A61M 5/31551* (2013.01); *A61M 5/31561* (2013.01);  
(Continued)

(58) Field of Classification Search  
CPC .......... A61M 2005/2407; A61M 5/24; A61M 5/31551; A61M 5/31583; A61M 5/28; A61M 2005/247  
USPC .......................................... 604/86, 201–207  
See application file for complete search history.

(56) References Cited

U.S. PATENT DOCUMENTS

| 2,842,126 A | 7/1958 | Brown |
| 3,401,693 A | 9/1968 | Cohen |

(Continued)

FOREIGN PATENT DOCUMENTS

| EP | 0288003 | 10/1988 |
| WO | 2008/031239 | 3/2008 |

OTHER PUBLICATIONS

International Search Report for Int. App. No. PCT/EP2010/066313, completed May 2, 2011.

(Continued)

*Primary Examiner* — Kevin C Sirmons  
*Assistant Examiner* — Deanna K Hall  
(74) *Attorney, Agent, or Firm* — McDonnell Boehnen Hulbert & Berghoff LLP

(57) ABSTRACT

The present invention relates to a drug delivery device for dispensing of a dose of a medicinal product, comprising, a housing, a drive mechanism comprising an axially displaceable piston rod to act on a piston of a cartridge containing the medicinal product to be dispensed, wherein the housing is adapted to support a piercing element which is adapted to penetrate a distal end face of the cartridge exclusively on demand. Furthermore, the drug delivery device comprises means for displacing the cartridge from a proximal stop position to a distal stop position in an axial direction and with respect to the housing, wherein in the distal stop position, the cartridge is connected to the piercing element and wherein in the proximal stop position, the cartridge is disconnected from the piercing element such that a fluid transfer between inside volume of the cartridge and the piercing element is interrupted.

20 Claims, 13 Drawing Sheets

(52) U.S. Cl.
CPC .. *A61M 5/31583* (2013.01); *A61M 2005/2407* (2013.01); *A61M 2005/2492* (2013.01); *A61M 2005/3103* (2013.01); *A61M 2005/3142* (2013.01); *A61M 2005/3152* (2013.01)

(56) References Cited

U.S. PATENT DOCUMENTS

| 2004/0111063 | A1 | 6/2004 | Botich | |
| 2006/0052747 | A1 | 3/2006 | Nishimura et al. | |
| 2006/0111063 | A1 | 3/2006 | Nishimura et al. | |
| 2009/0259195 | A1* | 10/2009 | Lin Lee | 604/195 |
| 2012/0184917 | A1* | 7/2012 | Bom et al. | 604/187 |

OTHER PUBLICATIONS

International Preliminary Report on Patentability for Int. App. No. PCT/EP2010/066313, mailed May 10, 2012.

* cited by examiner

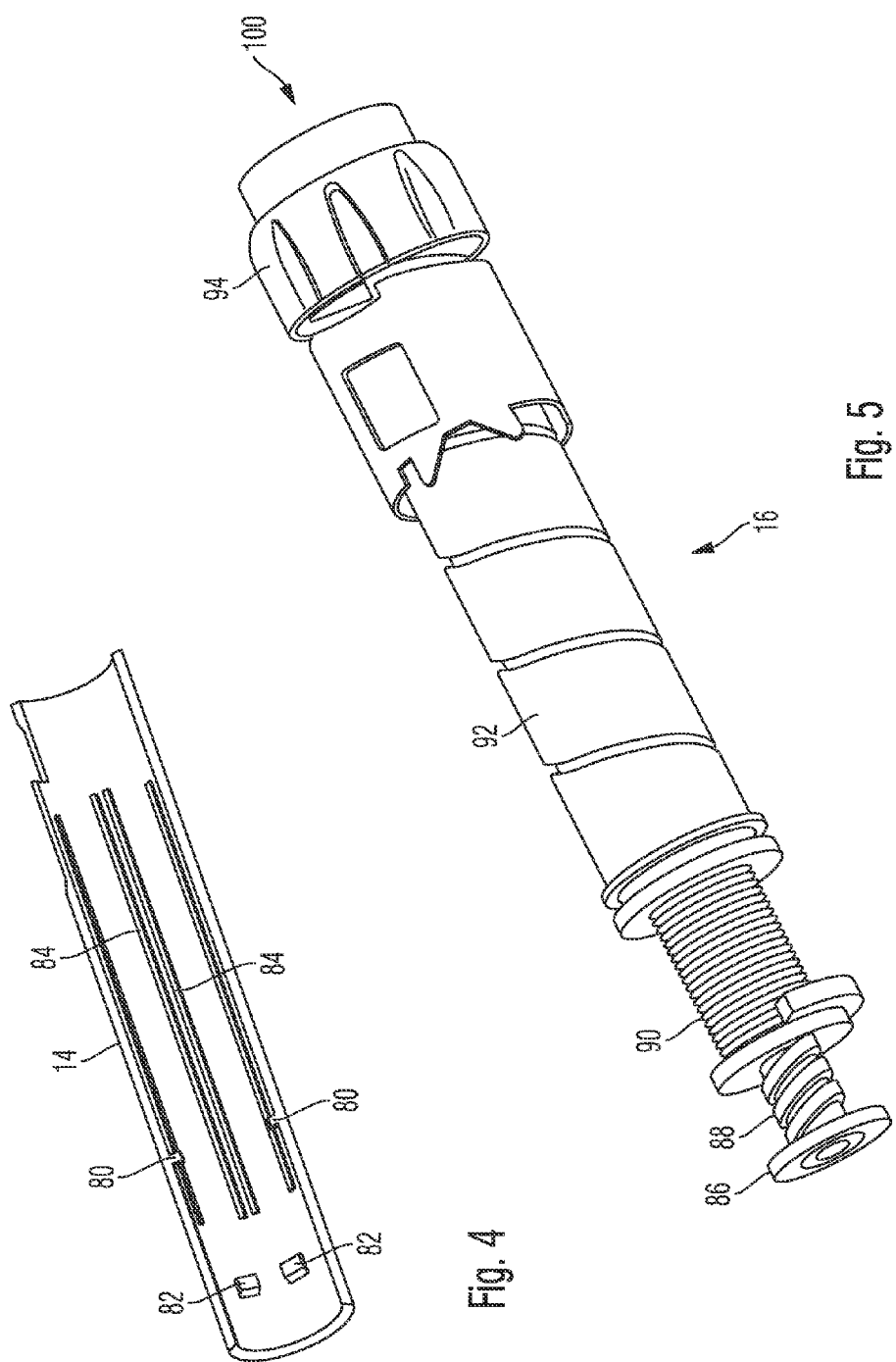

DRUG DELIVERY DEVICE

CROSS REFERENCE TO RELATED APPLICATIONS

The present application is a U.S. National Phase Application pursuant to 35 U.S.C. §371 of International Application No. PCT/EP2010/066313 filed Oct. 28, 2010, which claims priority to European Patent Application No. 09174670.1 filed on Oct. 30, 2009. The entire disclosure contents of these applications are herewith incorporated by reference into the present application.

FIELD OF INVENTION

The present invention relates to a drug delivery device such as a pen-type injector, to a cartridge to be removably arranged inside such drug delivery devices and to a corresponding drive mechanism, wherein a single or a number of pre-set doses of a medicinal product can be administered. In particular, the invention relates to such drug delivery devices being designed for self-administration of a medicinal product.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Pen-type injectors of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Also, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

The medicinal product to be dispensed by means of the drug delivery device is typically provided in a disposable or replaceable cartridge, such as a vial, ampoule or carpule comprising a slidably disposed piston to be operably engaged with a piston rod of a drive mechanism of the drug delivery device. By applying thrust to the cartridge's piston in distal direction, a predefined dose of the liquid drug can be dispensed and expelled from the cartridge.

Cartridges as they are typically used with drug delivery devices, in particular with pen-type injectors are typically sealed by means of as septum. Such a septum is commonly designed as a rubber stopper providing an air-tight seal but being pierceable by piercing elements such as needles or cannulae.

Typically, such drug delivery devices comprise a cartridge holder adapted to receive a cartridge which is hermetically sealed with such flexible and deformable septum. At its lower and distal end section, the cartridge holder can for instance be threadedly engaged with a needle mount. Said needle mount or needle holder typically comprises a correspondingly threaded cylindrical portion for releasably interconnecting needle holder and cartridge holder.

During assembly of the needle holder the proximally located tipped end of the needle penetrates the septum of the cartridge. In this way, a fluid-transferring connection for the purpose of dose dispensing can be established.

In particular, during dispensing of a dose of the medicinal fluid contained in the cartridge, a respective fluid pressure is built-up. During a dose dispensing procedure the piston is subject to an axial squeezing and/or the septum might become subject to an axial expansion. Due to their elastic properties, septum and/or piston may store elastic energy during dose dispensing. Right after completion of a dose dispensing procedure, the septum and/or the piston typically relax to their initial configuration, because the fluid pressure inside the cartridge drops. Since the piston is in an abutment position with a distally arranged bearing of a piston rod, relaxation of the piston inevitably leads to an expansion of the piston in distal direction. Similarly, the expanded section of the septum retracts into the cartridge.

Both relaxing phenomena may in turn lead to a post-dispensing built-up of a non-negligible fluid pressure and, as a consequence, a certain amount of medicinal fluid may be supplementary expelled from the cartridge, which can be typically observed in the form of droplet formation at the distal tip of the needle, which remains in permanent fluid-transferring contact with the inner volume of the cartridge as long as the needle assembly remains connected with the cartridge holder.

Additionally, such droplet formation may occur during assembly of the needle mount to the cartridge holder, especially, when the inside pressure of the cartridge is larger than ambient pressure. Since some dispensable medicinal products like Insulin or Erythropoietin (EPO) have to be stored refrigerated, a non-negligible pressure increase may for instance arise due to thermal expansion, e.g. if the cartridge or the drug delivery device is kept in a non-refrigerated environment at least for a while.

SUMMARY

It is therefore an object of the present invention, to provide a drug delivery device which is less prone to droplet-generation, preferably both during needle assembly as well as after completion of a dose dispensing procedure. The invention further focuses on a reliable, cost-efficient mechanism for droplet prevention, which is easy to assemble and which can be universally applied to a variety of drive mechanisms for drug delivery devices.

The present invention provides a drug delivery device for dispensing of a dose of a medicinal product. The drug delivery device comprises a housing, typically a two-component housing having a proximally located main housing section and a distally located cartridge holder section, wherein the main housing section is substantially adapted to receive a drive mechanism of the drug delivery device and wherein the cartridge holder section is adapted to hold and to receive a cartridge that contains the medicinal product to be dispensed by the drug delivery device, preferably by injection.

The drive mechanism of the drug delivery device comprises an axially displaceable piston rod which operably engages and at least unidirectionally acts on a piston of a cartridge. The cartridge itself is preferably designed as disposable and replaceable article. Generally, the cartridge is not a constituent of the drug delivery device. Only in such embodiments, wherein the entire drug delivery device is constructed as a disposable device, the cartridge may be regarded as integral component of the drug delivery device.

The cartridge is typically designed as vial, carpule or ampoule. It is filled or it is to be filled with a medicinal product to be dispensed a well-defined way, typically in multiple doses.

The cartridge containing a liquid drug like Heparin or Insulin is hermetically sealed at its distal end face, typically by means of a flexible and deformable septum, which is penetrable by a piercing element, such as an injection needle or a cannula. The housing, in particular the distal end section of the cartridge holder section, is adapted to support a replaceable piercing element, which is to be coupled to the interior of the cartridge in a fluid transferring way at least for dose dispensing.

The present invention is particularly characterized by means for reversibly displacing the cartridge in axial direction with respect to the housing. In particular, the cartridge is at least displaceable from a proximal stop position to a distal stop position. Transition of the cartridge from the proximal stop position to the distal stop position is typically characterized by a linear axial movement along the axis of symmetry of the housing, i.e. along the housing's long axis. In the present context, reversible displacement of the cartridge means, that the cartridge is intended to be displaced in axial direction back and forth between its proximal and distal stop position.

In the proximal stop position, the cartridge is disconnected from the piercing element, preferably such that a fluid-transferring coupling of piercing element and inside volume of the cartridge is interrupted. However, in its distal stop position, the cartridge is connected to the piercing element in a fluid transferring way. At least when reaching its distal stop position, the distal end face of the cartridge, i.e. its septum, is penetrated and intersected by the piercing element.

Axial displacement of the cartridge inside the housing is preferably activated and controlled by the drive mechanism. Drive mechanism and cartridge are therefore operably engaged. It is of particular benefit, when the cartridge is in its proximal stop position during assembly of the piercing element and the housing. In this way, the piercing element does not intersect or penetrate the cartridge's septum prior injection. Septum penetration preferably occurs at a later stage, preferably during a dose dispensing action, in which the cartridge and the drive mechanism in its entirety become subject to a distally directed axial displacement.

Furthermore, the present invention also intends to provide a self-actuated disconnecting of piercing element and cartridge as soon as a dose dispensing procedure has terminated. Hence, the means for displacing the cartridge are adapted to displace the cartridge bi-directionally on demand. Since the cartridge can be disconnected from the piercing element after termination of a dose dispensing procedure, the phenomenon of post-dispensing droplet generation, which might be due to relaxation processes of elastic components of the cartridge can be effectively eliminated or at least remarkably reduced.

According to a preferred embodiment of the invention, the means for displacing the cartridge are adapted to reversibly displace the cartridge in the housing between the proximal and the distal stop position. Therefore, the cartridge is displaceably supported in the housing in axial direction in a bi-directional way, that allows for a selective connecting and disconnecting of cartridge and piercing element, respectively.

In a further preferred embodiment, the cartridge is spring-supported in distal direction against a distal end section of the housing. Here, a spring element, preferably a compression spring element, is disposed inside the cartridge holder in such a way, that the spring element is compressed and stores mechanical energy during a distally directed displacement of the cartridge. This compression spring element serves to provide a self-actuating disconnecting of cartridge and piercing element, in particular after completion of a dose dispensing procedure.

In another preferred embodiment, the drive mechanism is adapted to selectively act on a proximal end section of the cartridge's sidewall and/or to act on a proximal end face of the piston. According to this embodiment, the drive mechanism provides multiple functions. By way of the drive mechanism, the cartridge itself can be displaced in distal direction with respect to the housing or the cartridge holder. Once the cartridge has reached its distal stop position, the drive mechanism is furthermore adapted to exert distally directed thrust to a proximal end face of the cartridge's piston in order to distally displace the piston for the purpose of expelling of a pre-defined amount of the liquid medicinal product.

Preferably, a dose injection process splits in two subsequent steps. In a first step, the cartridge is displaced in distal direction until it rests in its distal stop position. In a subsequent second step, further distally directed thrust is selectively directed onto the cartridge's piston for conducting the dose dispensing. Here, the drive mechanism selectively provides distal displacement of the cartridge with respect to the housing as well as distal displacement of the cartridge's piston with respect to the sidewall of the cartridge. These different ways of relative displacement of cartridge and piston are preferably conducted sequentially but not combined. In this way, it can be ensured, that the piston starts to move with respect to the cartridge's sidewall when the cartridge itself is in its distal stop position, in which the cartridge is coupled to an injection needle or cannula in a fluid-transferring way.

According to a further preferred embodiment, the piston rod is radially guided by a clutch assembly, which is adapted to transfer a distally directed thrust either to the cartridge's sidewall or to the piston of the cartridge. Depending on the respective configuration of the clutch, a distally directed motion of a piston rod is either transferred to a distally directed displacement of the cartridge as a whole or to a distally directed displacement of the cartridge's piston, wherein the cartridge itself is axially fixed or interlocked with respect to the housing of the drug delivery device.

According to another preferred embodiment of the invention, the clutch assembly is axially displaceably guided in the housing. This way, cartridge, clutch assembly as well as drive mechanism may become subject to a combined distally or proximally directed displacement for connecting or disconnecting cartridge and piercing element. Preferably, also the clutch assembly is axially displaceable between a proximal and a distal stop position, that are correlated to respective distal and proximal stop positions of the cartridge.

In a further preferred aspect, the clutch assembly is secured against rotation with respect to the housing. The housing, typically of cylindrical or tubular shape may comprise retention means at its inner surface of the sidewall, whereas the clutch means may comprise corresponding retention means at is outer circumference.

In another embodiment, the clutch assembly is selectively convertible into a locking and a release configuration. In its locking configuration, the clutch assembly impedes a rotation of the piston rod with respect to the housing. Typically, the clutch assembly might be threadedly engaged or otherwise rotatably engaged with the clutch assembly. In its locking configuration, the clutch assembly substantially impedes a rotation of the piston rod relative to the clutch assembly. Therefore, a distally directed displacement of the piston rod directly transfers to the clutch assembly and to the sidewall of the cartridge.

In its release configuration, the clutch assembly allows for an axial movement of the piston rod with respect to the cartridge's sidewall. Here, a distally directed displacement of the piston rod directly transfers to a respective displacement of the cartridge's piston.

In embodiments, wherein the clutch assembly and the piston rod are threadedly engaged, the piston rod might be subject to a combined axial and rotational displacement with respect to the clutch assembly.

Switching of the clutch assembly between a locking and a release configuration might be triggered by an axial compression of the clutch assembly itself. For instance, the clutch assembly may be in locking configuration per default setting and may enter into release configuration when reaching its distal stop position in the housing.

According to a further preferred embodiment, the clutch assembly comprises a first and a second clutch element and an intermediary spring element, which is adapted to axially separate first and second clutch elements from each other. Consequently, the spring element sandwiched between first and second clutch elements serves to increase the axial expansion of the clutch assembly. First and second clutch elements are therefore axially biased by said spring element.

In a further modification, the piston rod is threadedly engaged with both, the first and with the second clutch element. First and second clutch elements therefore comprise threaded through openings to receive the piston rod. Preferably, said through openings of first and second clutch elements comprise identical threads. Hence, the piston rod is retained and rotatably secured when first and second clutch elements are separated from each other under the effect of the intermediary spring element. The threaded engagement of the clutch elements and the piston rod is preferably of self-inhibiting type. It may even be of non-self-inhibiting type due to a clamping achieved by the spring-biased displacement of first and second clutch elements. This way, a rotational movement of the piston rod with respect to the clutch means or with respect to the housing can be effectively prevented.

Since the clutch assembly itself is rotatably secured with respect to the housing, in its locked configuration, the clutch assembly allows for an axial displacement of the piston rod, typically combined by a respective and identical axial displacement of the clutch assembly.

According to a further preferred embodiment, the first clutch element comprises at least one axially extending strut section, which at least partially and radially surrounds the second clutch element. Hence, first and second clutch elements are arranged in an at least partially interleaved manner. The at least one axially extending strut section of the first clutch element is also operably engaged with the sidewall of the cartridge. In typical embodiments, first and second clutch elements are arranged and configured in a nested way. Preferably, the first clutch element comprises at least two or even more strut sections being regularly arranged across the circumference of the first clutch element.

Said axially and preferably distally directed strut sections form interstices at the circumference of the first clutch element, that are adapted to receive correspondingly shaped radial disk-like protrusions of the second clutch element.

The spring element, which can be designed as spring washer, disk spring or as a disk-like washer comprising spring arms to be axially biased, is preferably at least rotatably locked with either the first and/or second clutch element.

In another preferred embodiment of the invention, the second clutch element comprises at least one projection radially extending between adjacent strut sections of the first clutch element. During displacement of the cartridge to its distal stop position, said projection axially abuts against a stop element, typically, when said second clutch element reaches its distal stop position. The stop element, which can be designed as a component of the housing, impedes a further distally directed displacement of the second clutch element. In the course of a continuous distal displacement of the piston rod, the intermediary spring element then becomes subject to compression until the clutch assembly is transferred in its release configuration.

In response to the clutch release, the piston rod is free to rotate, thereby becoming subject to an axial displacement with respect to the clutch assembly. Since the piston rod preferably remains in permanent contact to a proximal end face of the piston by means of a bearing, a distally directed and externally provided force acting on the drive mechanism splits into first and second distally directed thrust, that acts on the sidewall of the cartridge and on the piston, respectively.

If at the end of a dose dispensing procedure, an externally applied force drops below a predefined threshold, the spring-biased cartridge will return to its proximal stop position. This movement may be accompanied by a respective mutual axial displacement of first and second clutch elements leading to a rotation-impeding locking of the clutch assembly.

Hence, at the end of a distally directed displacement of the cartridge, the radially extending projections of the second clutch element abut against a stop element of the housing, such that first and second clutch elements are brought together against the action of the intermediary spring element. Consequently, the clutch assembly releases. In the opposite way, as soon as the thrust exerted on the drive mechanism drops below a predefined threshold, the spring element of the clutch as well as the spring element intermediary arranged between distal end sections of housing and cartridge serve to restore the device to its initial or default configuration.

According to a further preferred embodiment, the stop element to be operably engaged with the second clutch element is designed as an integral component of either the main housing section or the cartridge holder section. In a preferred embodiment, the housing of the drug delivery device comprises two components, namely a main housing section and a cartridge holder section. Here, a proximal end section of the cartridge holder section is assembled in a distally located receptacle of the main housing section. Furthermore, a proximal end face of the cartridge holder section serves as an axial stop element. Hence, by assembling main housing section and cartridge holder section in a nested or interleaved manner, a circumferential stopper can be generated to be operably engaged with the clutch element.

In a further aspect, the invention also provides a cartridge to interact with and to be inserted into a drug delivery device according to the present invention. The cartridge comprises a proximal end section sealed by an axially displaceable piston. Preferably, it is at least partially filled with the medicinal product to be dispensed. The cartridge further comprises a sealed distal end section, which preferably comprises a bottle-neck-like shape. The distal end section of the cartridge is sealed by a seal, such like a septum, being secured to the sidewall of the cartridge by means of e.g. a fixing sleeve. The fixing sleeve, which is preferably designed as a clamping or crimping element made of metal comprises a centric through opening, through which the piercing element is to be guided for piercing and penetrating the seal.

The diameter or the surface of the fixing sleeve's through opening is smaller than 30%, preferably smaller than 20%, more preferably smaller 10% and most preferably smaller than 5% of the diameter or cross section of the fixing sleeve.

In other words, the diameter or the surface of a pierceable section of the seal is particularly smaller than 30%, 20%, 10% preferably smaller than 5% of the diameter or cross section confined by the tubular section of the sidewall of the cartridge.

Such small through openings of the fixing sleeve can in fact be realized because the piercing element is already in its final assembly position when the cartridge is subject to a distal displacement in the direction to its distal stop position. Due to the radial guiding of the cartridge inside the housing, a sufficiently precise piercing of the seal can be achieved.

Therefore, the pierceable area of the cartridge's distal end section can be remarkably reduced compared to conventional liquid drug-containing cartridges. Since the effective surface of the septum is drastically reduced, the septum also becomes less prone to a distally directed protrusion during a dose dispensing procedure. Also by downsizing the piercable seal of the cartridge, post-dispending droplet generation can be counteracted.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the pertinent art that various modifications and variations can be made to the present invention without departing from the spirit and scope of the invention. Further, it is to be noted, that any reference signs used in the appended claims are not to be construed as limiting the scope of the present invention

BRIEF DESCRIPTION OF THE FIGURES

Without limitation, the present invention will be explained in greater detail below in connection with preferred embodiments and with reference to the drawings in which:

FIG. 4 illustrates the main housing section partially cut, FIG. 5 illustrates the drive mechanism in a perspective view.

DETAILED DESCRIPTION

Figure 1:
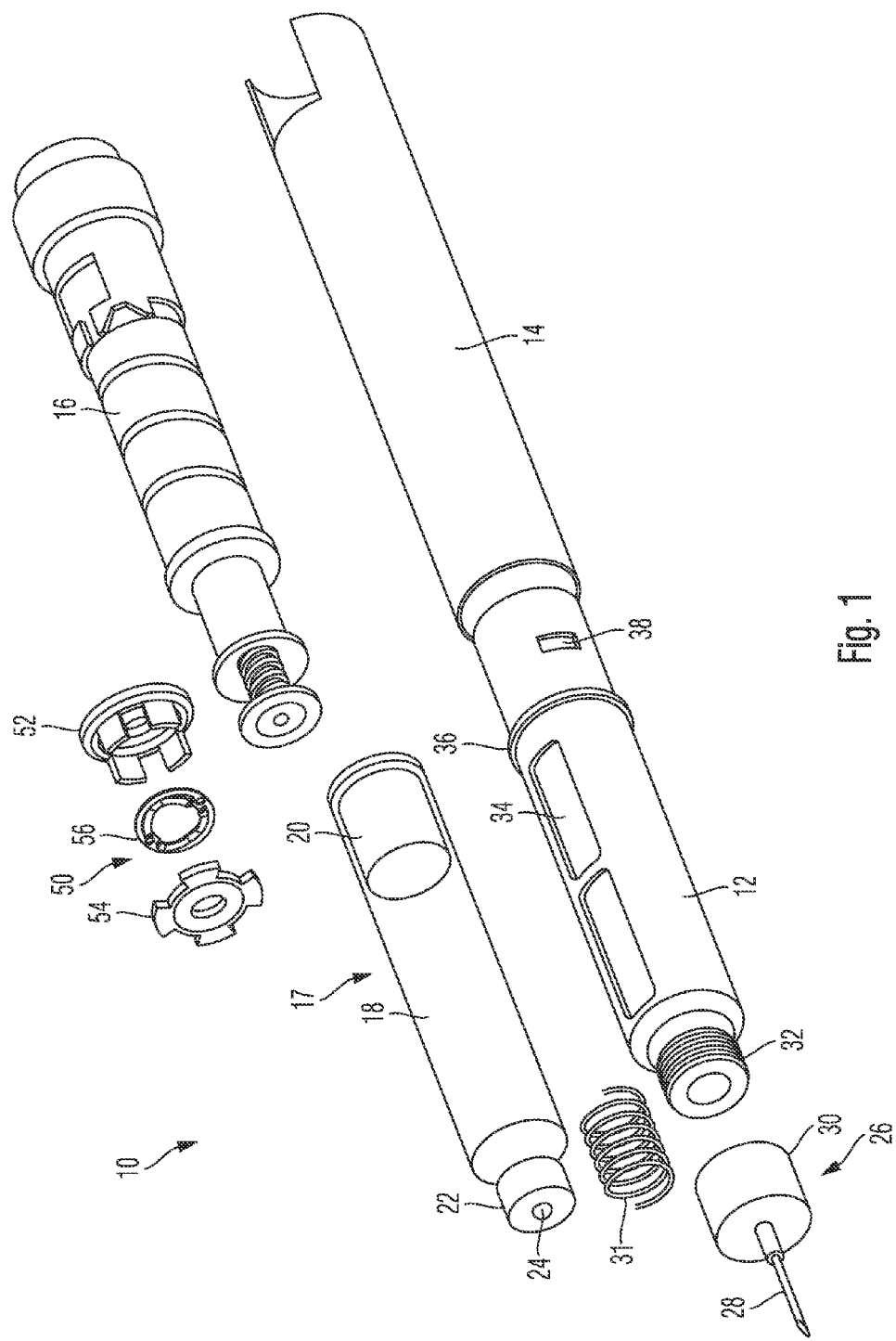
FIG. 1 illustrates the various components of the drug delivery device in a perspective exploded illustration.

The drug delivery device 10 as illustrated in FIG. 1 in an exploded view comprises a two-component housing having a proximal main housing section 14 and a distally located cartridge holder section 12. The cartridge holder section 12 is adapted to receive a cartridge 17, which is typically filled with a fluid medicinal product. The cartridge 17, in particular its sidewall 18, is of tubular shape and receives a moveable piston or bung 20 which seals the interior of the cartridge 17 in proximal direction. In distal direction, the cartridge 17 or the cartridge wall 18 comprises a stepped down neck portion or bottle neck portion, which is sealed by a septum 24.

Figure 13:
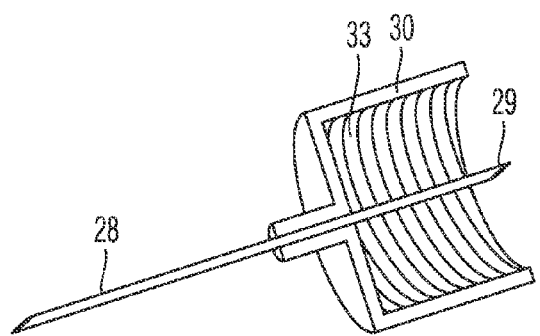
FIG. 13 shows the needle mount partially cut.

The septum 24 in turn is fixed to the cartridge wall 18 by means of a fixing sleeve 22, typically designed as an aluminium crimp. A needle assembly 26 having a cupped needle mount 30 can be screwed on a threaded stepped down portion 32 at the distal end of a cartridge holder section 12. As illustrated in FIG. 13, the piercing element or injection needle 28 is permanently connected with the needle mount 30. The needle mount 30 at its inner sidewall comprises a thread 33 corresponding with the thread of a distal end section 32 of the cartridge holder 12.

Figure 14:
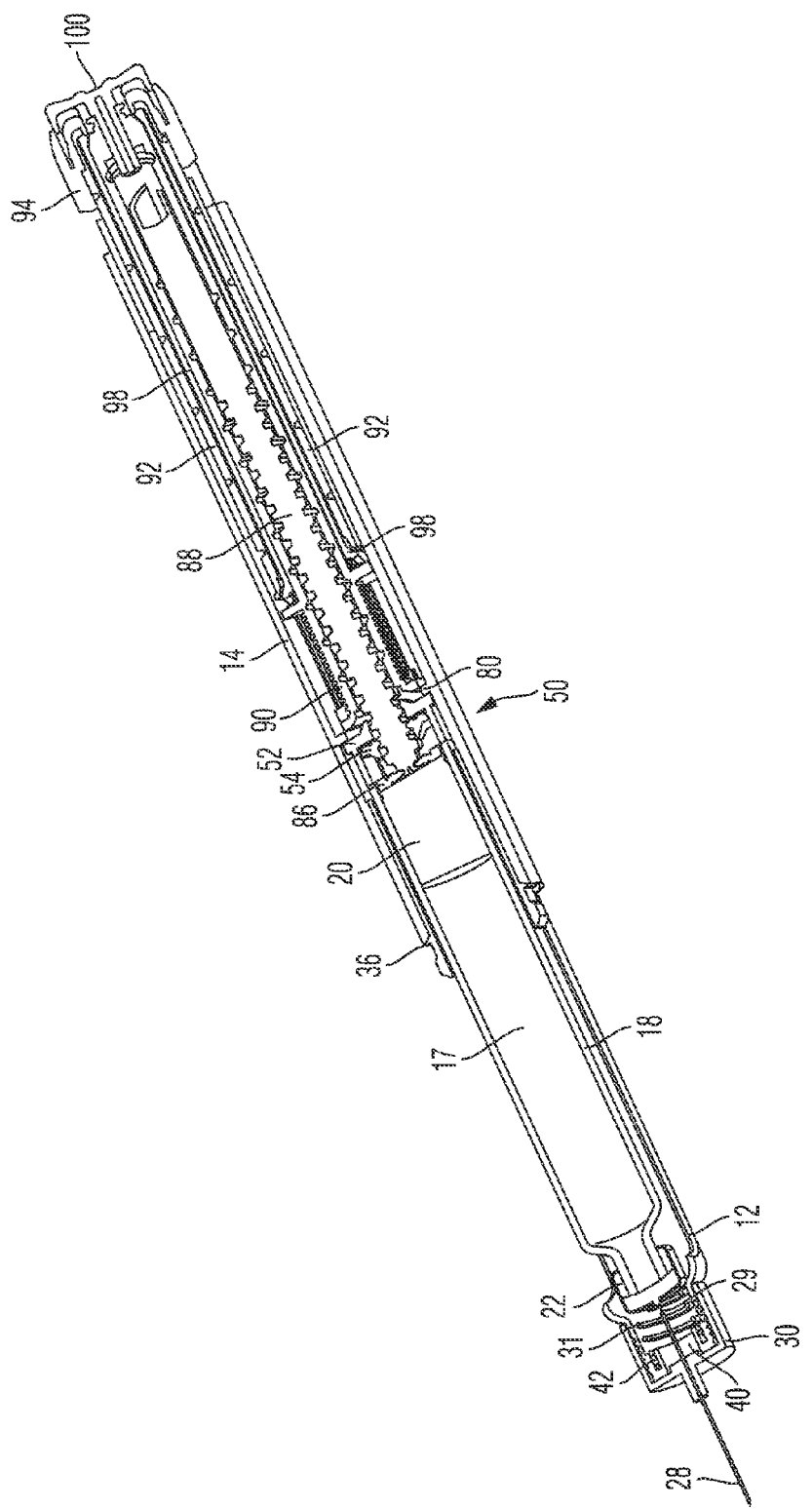
FIG. 14 illustrates the entire drug delivery device in a cross-sectional view in a default configuration.
Figure 16:
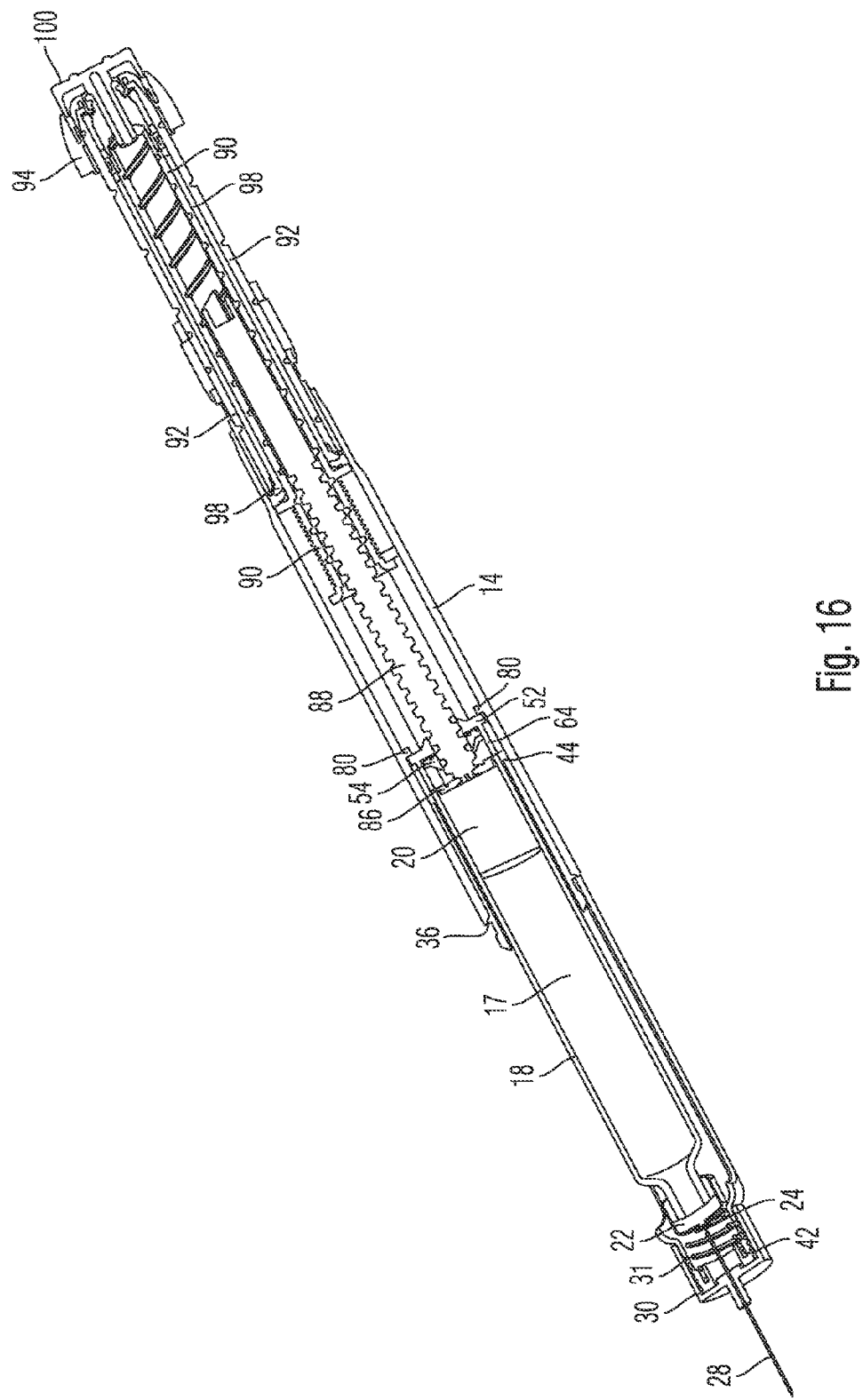
FIG. 16 is illustrative of the pen-type drug delivery device during or after setting of a dose.

The needle 28 extends in distal as well as in a proximal direction. With a proximally located tipped end 29, the injection needle 28 may penetrate the septum 24 of the cartridge 17. The cartridge 17 itself is spring-biased and axially displaceably supported inside the cartridge holder section 12 as illustrated in FIGS. 14 and 16. For this purpose, the distal end section of the cartridge holder section 12 comprises a proximally directed and inwardly extending shaft 40 that forms a slit-like circumferential receptacle 42 to receive the helical compression spring 31.

The compression spring 31 abuts against the distal end face of the cartridge 17. In particular, the spring 31 abuts with the fixing sleeve 22 of the cartridge. The axially inwardly extending shaft 40 may additionally serve as a stopper to delimit a distally directed displacement of the cartridge 17. Hence, axial extension of the shaft 40 may specify the distal stop position of the cartridge 17 with respect to the housing component 12.

The two housing components 12, 14 are adapted to be assembled in a nested or interleaved way. As illustrated in FIGS. 1 and 14 for example, the cartridge holder section 12 comprises an annular rim 36, that abuts with a distal end face of the main housing component 14. Moreover, the cartridge holder section 12 comprises numerous recesses 38 that are adapted to receive radially inwardly protruding catch elements 82 of the tubular shaped main housing section 14 as they are apparent from in FIG. 4. In this way, cartridge holder section 12 and main housing section 14 can be positively and releaseably engaged with respect to each other.

Figure 2:
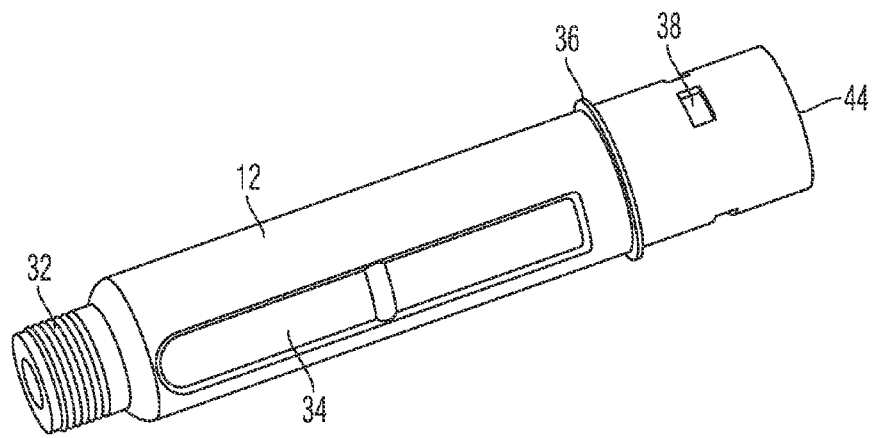
FIG. 2 shows the cartridge holder section in a perspective view.
Figure 3:
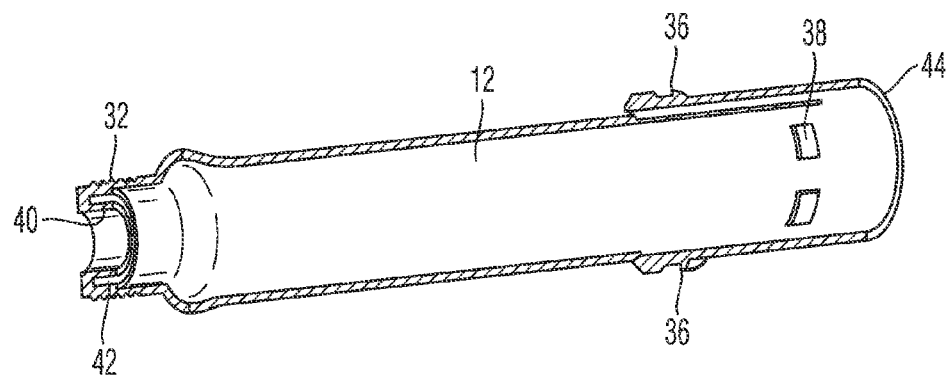
FIG. 3 shows the cartridge holder section in a partially cut view.

As further illustrated in FIGS. 1 and 2 the cartridge holder section 12 comprises an inspection window 34, which allows to visually control the filling level of the cartridge 17.

The drug delivery device 10 further comprises a clutch assembly 50 having a first clutch element 52, a second clutch element 54 and an intermediary spring element 56. The main housing section 14 is generally adapted to house the drive mechanism 16, which is separately illustrated in FIG. 5. The drive mechanism 16 comprises a piston rod 88 and a drive sleeve 90 threadedly engaged with the piston rod 88. Furthermore, the drive mechanism 16 comprises various clutch means, e.g. a clutch sleeve 98 arranged between an outer dose dial sleeve 92 and a drive sleeve 90. Furthermore, the drive mechanism 16 comprises a dose dial button 94 that allows to select and to set a predefined dose.

By way of the proximally located dose button 100, distally directed thrust can be exerted to the entire drive mechanism 16. The drive mechanism 16 illustrated in the present embodiment is almost identical to the drive mechanism of a pen-type injector as already known from WO 2004/078241 A1, which is hereby entirely incorporated by reference.

Bearing 86 and piston rod 88 are preferably positively locked, wherein the bearing 86 remains free to rotate with respect to the piston rod's 88 long axis. Said bearing 86 is further adapted to abut against a proximal end face of the cartridge's piston 20 and to transfer thrust to the piston 20 for expelling a pre-defined dose of the medicinal product from the cartridge 17.

The piston rod 88 comprises a distal thread, which is engaged with the through openings 58, 60 of first and second clutch elements 52, 54. Even though not explicitly illustrated, the piston rod 88 further comprises a proximal thread engaged with a corresponding inner thread of the drive sleeve 90. Typically, proximal thread and distal thread of the piston rod 88 are oppositely handed and comprise different leads.

In preferred embodiments, the threaded engagement of the piston rod 88 and the drive sleeve 90 is of non-self-locking type. In this way, an axially directed displacement of the drive sleeve 90 leads to a respective rotation of the piston rod 88 and due to the threaded engagement of piston rod 88 and the clutch assembly 50 to a respective relative axial displacement of piston rod 88 and sidewall 18 of the cartridge 17, when the cartridge 17 is in its distal stop position.

Figure 6:
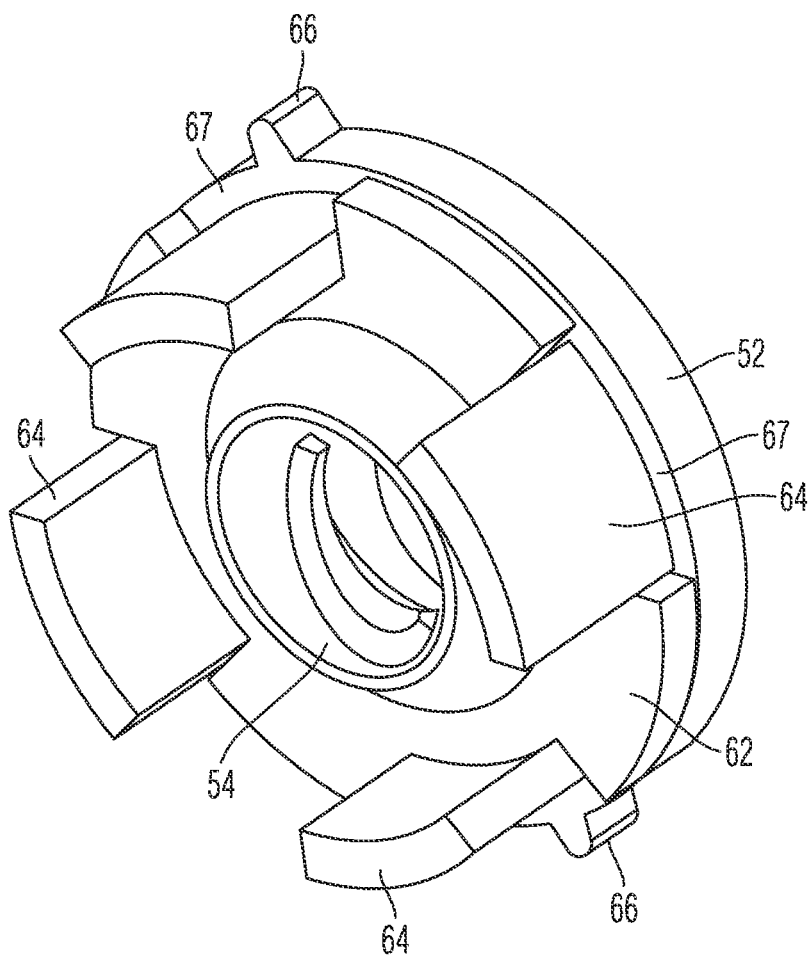
FIG. 6 is illustrative of the clutch assembly.
Figure 7:
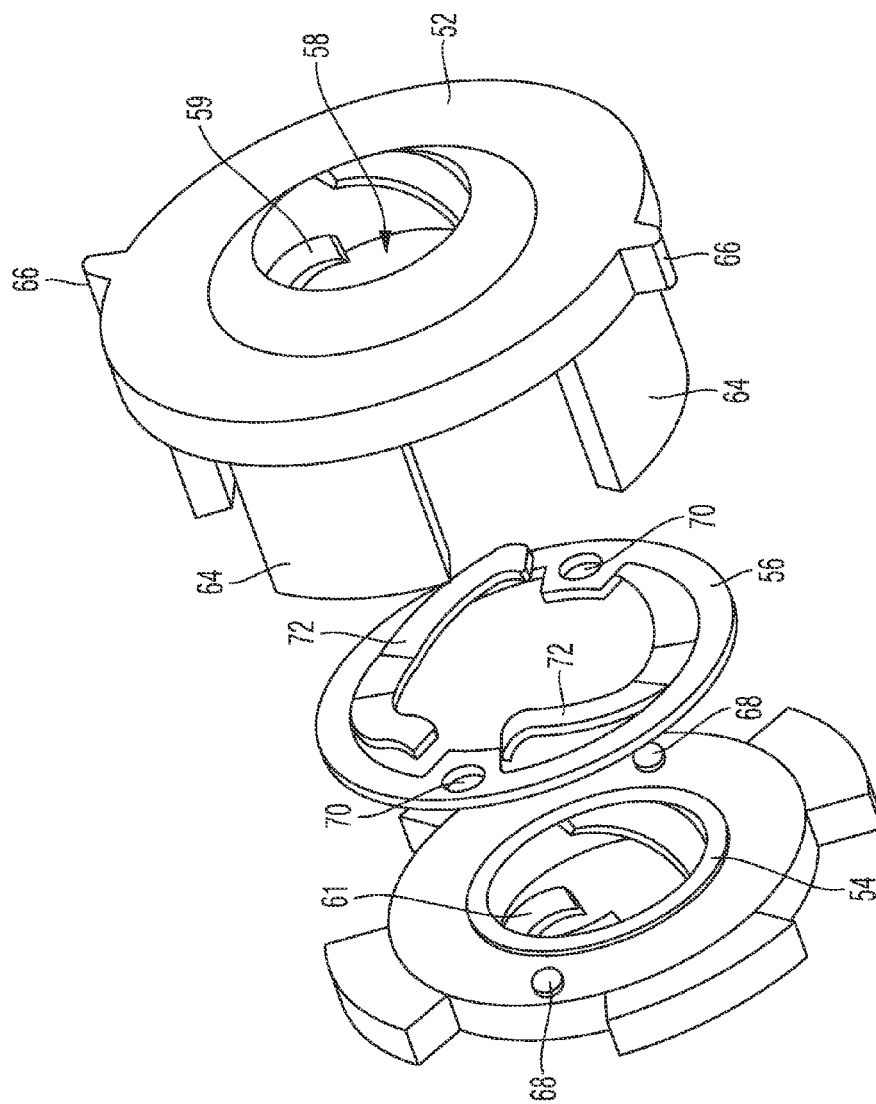
FIG. 7 shows the clutch assembly in an exploded view.
Figure 8:
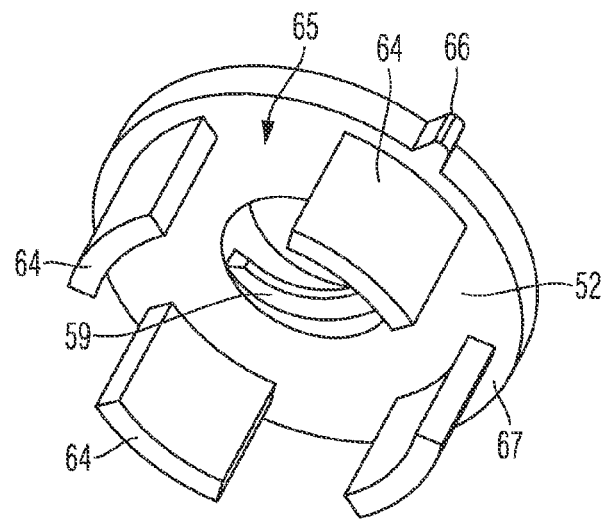
FIG. 8 shows the first clutch element in a perspective illustration.
Figure 9:
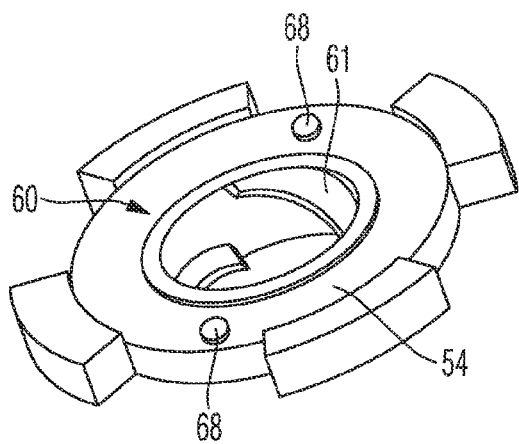
FIG. 9 is illustrative of the second clutch element as seen from proximal direction and FIG. 10 shows the second clutch element as seen from a distal point of view, FIG. 11 perspectively illustrates the intermediary spring element.
Figure 10:
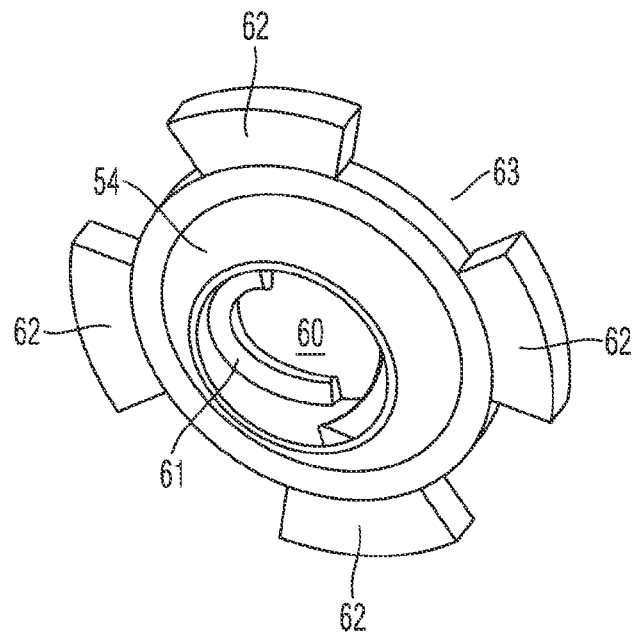
Figure 11:
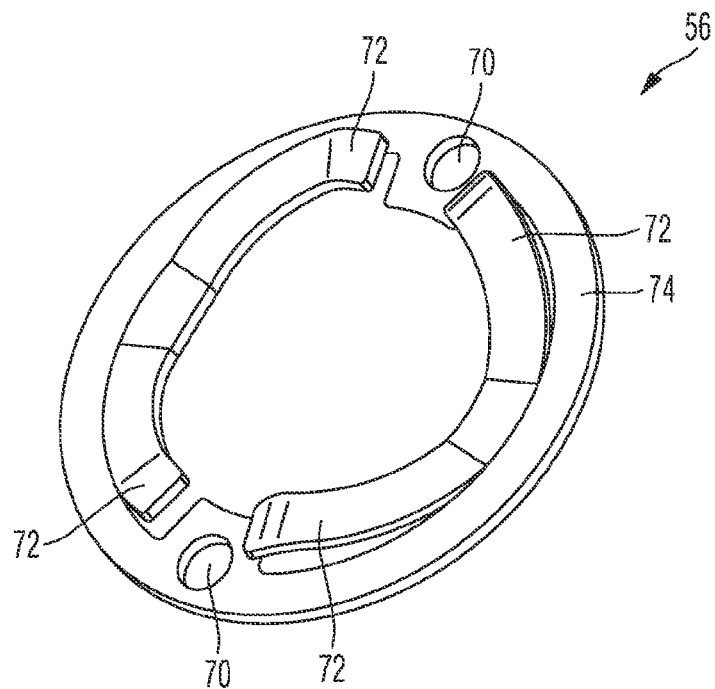
Figure 12:
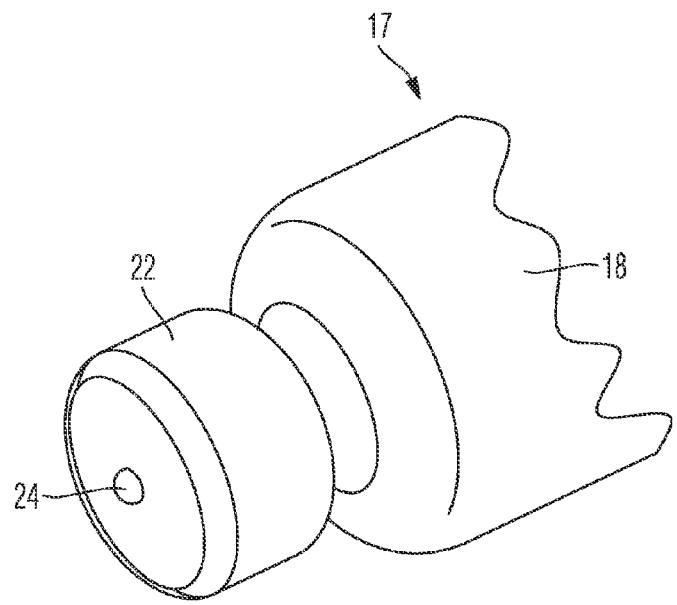
FIG. 12 illustrates the distal end section of the cartridge in an enlarged perspective view.

In FIGS. 6 through 10, the clutch assembly 50 is illustrated in detail. The clutch assembly 50 comprises a first clutch element 52 and a second clutch element 54. Both clutch elements 52, 54 are of disk-like shape and comprise co-linearly arranged threaded through openings 58, 60, as indicated in FIGS. 7 and 10. Through opening 58 of the first clutch element 52 comprises an inner thread 59 and through opening 60 of the second clutch element 54 comprises an inner thread 61. Both threads 59, 61 substantially comprise the same lead. Threads 59 and 61 further correspond to the outer thread of the piston rod 88.

The first clutch element 52 comprises two diametrically arranged and radially extending protrusions 66 at its outer circumference. With these protrusions 66, the first clutch element 52 is secured against rotation inside the main housing section 14. At its inner sidewall, main housing section 14 comprises two oppositely arranged and axially extending grooves 84 adapted to receive the protrusions 66 of the first clutch element 52. In this way, the first clutch element 52 and the entire clutch assembly 50 become axially displaceable but rotatably locked with respect to the housing 14.

The first clutch element 52 further comprises four regularly arranged strut sections 64 that extend in distal direction. Said strut sections 64 are integrally formed with the disk-shape section of the first clutch element 52 which comprises the threaded through opening 58. The strut sections 64 are of substantially quadratic or rectangular shape. They are further arranged near the outer circumference of the first clutch element 52. The strut sections 64 are shifted radially inwards, such that a socket 67 forms between the outer edge of the clutch element 52 and its strut sections 64, respectively. Moreover, the strut sections 64 are arc-shaped according to the substantially circular circumference of the first clutch element 52.

Figure 15:
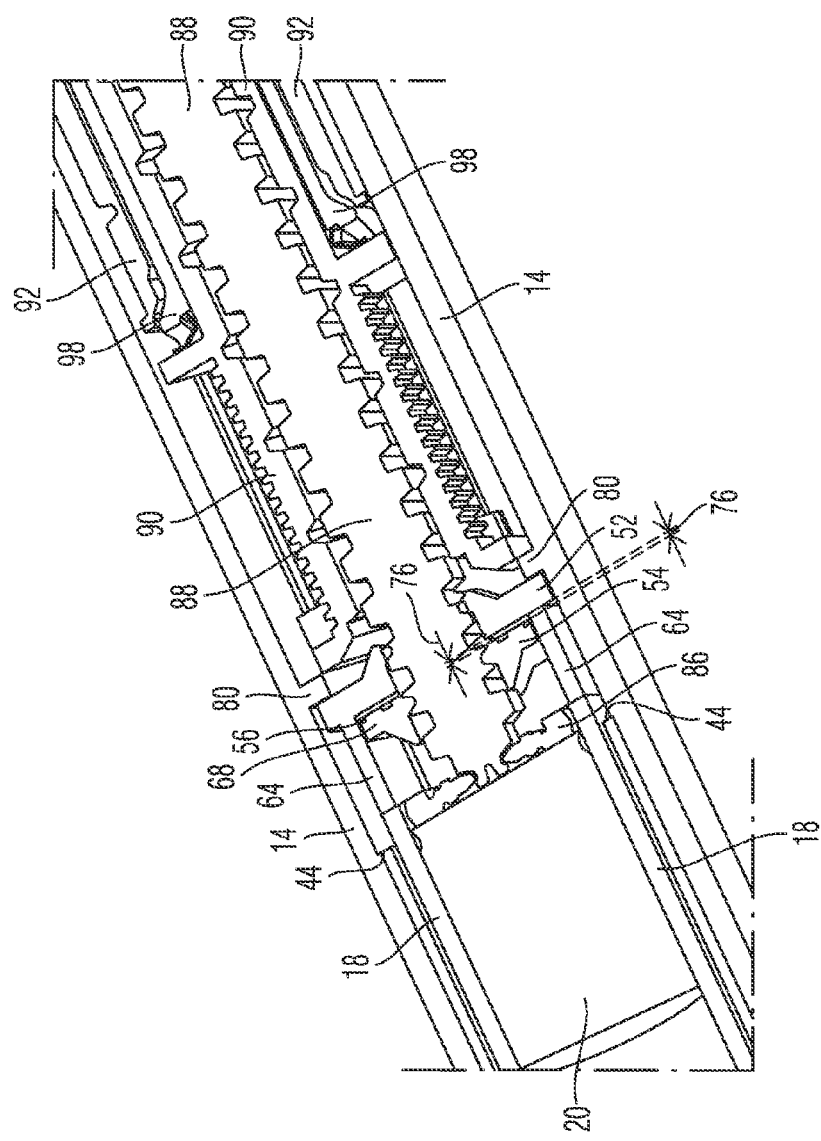
FIG. 15 illustrates an enlarged part of the configuration according to FIG. 14 with the clutch assembly in locking configuration.
Figure 17:
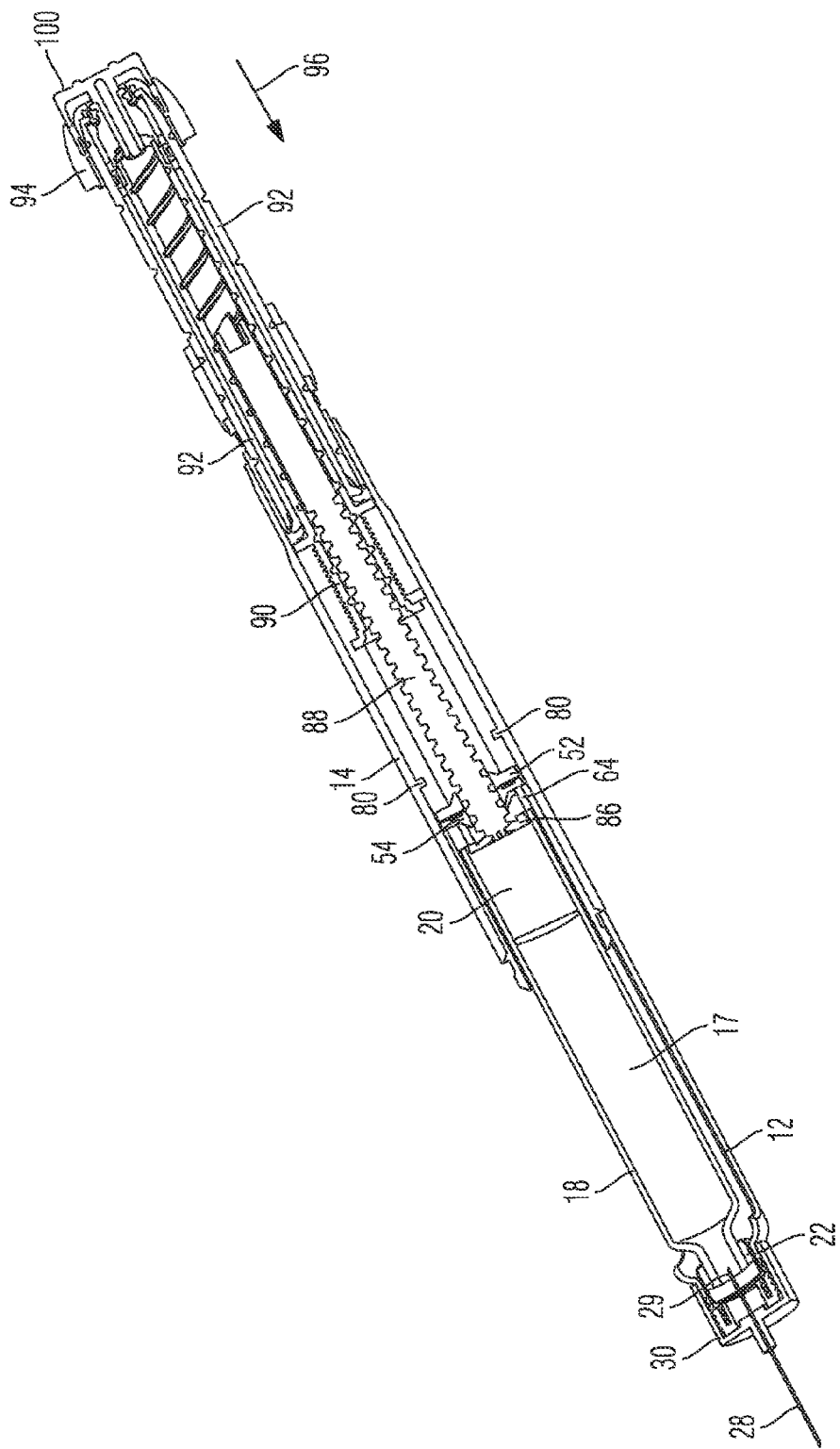
FIG. 17 shows the drug delivery device according to FIG. 16 but with cartridge and clutch assembly in their distal stop positions and FIG. 18 shows an enlarged extract of FIG. 17, wherein the released clutch assembly is in distal stop position.
Figure 18:
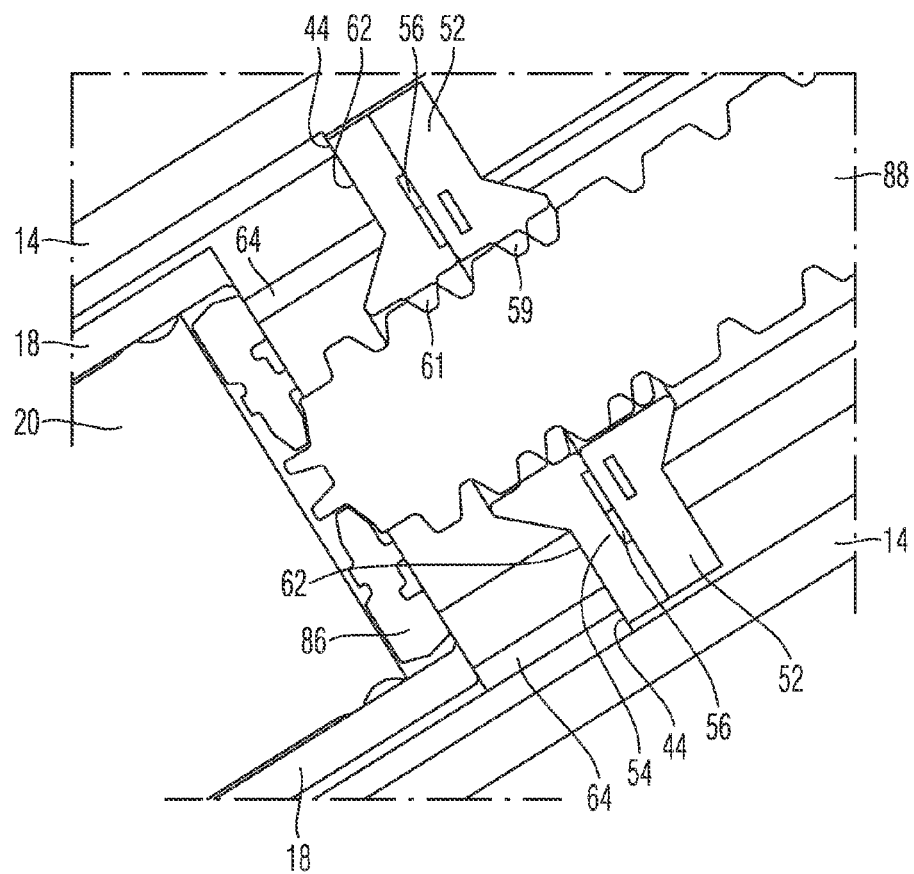

As can be further seen from FIGS. 15 and 18, the strut sections 64 in distal direction abut against a proximal end face of the cylindrical sidewall of the cartridge. Hence, by way of the strut sections 64, externally applied thrust can be transferred exclusively to the sidewall 18 of the cartridge 17 for the purpose of displacing the cartridge 17 in its distal stop position, which is illustrated in FIG. 17.

As further illustrated in FIGS. 6 through 10, the strut sections 64 of the first clutch element 52 are spaced apart from each other and form clearances 65 that are adapted to receive radially extending wedge-shaped protrusion 62 of the disk-shaped second clutch element 54. In this way, first and second clutch elements 52, 54 are displaceably arranged in axial direction. But first and second clutch elements 52, 54 are rotatably secured with respect to each other.

Correspondingly, also the second clutch element 54 comprises four recesses 63 between the radially extending and wedge-shaped protrusions 62. In an assembly configuration, as illustrated in FIG. 6, these recesses 63 are adapted to receive the strut sections 64 of the first clutch element 52.

Between first and second clutch elements 52, 54 a disk-shaped compression spring 56 is arranged. The compression spring 56 comprises an outer collar intersected by two oppositely arranged receptacles 70. By way of the two receptacles 70, the spring element 56 can be rotatably secured with the second clutch element 54, in particular, when the proximally extending pins 68 of the second clutch element 54 extend through the through openings 70 of the spring element 56. Radially inwardly, the spring element 56 comprises four spring arms 72 that extend in proximal direction and abut against an inner surface of the first clutch element 52. Per default and if no external forces are applied, the spring element 56 will keep first and second clutch elements 52, 54 in an axial distance 76 as illustrated in FIG. 15. Since both clutch elements 52, 54 are threadedly engaged with the piston rod 88, by way of separating first and second clutch elements 52, 54, the piston rod 88 can be rotatably secured and clamped with the clutch assembly 50.

Since the first clutch element 52 is in turn rotatably secured with respect to the main housing section 14, consequently in said locking configuration, a rotational movement of the piston rod 88 with respect to the housing 14 is inhibited. Therefore, if the clutch assembly 50 is in its locking configuration, any distally applied thrust 96 acting on the dose button 100 leads to an axial and distally directed displacement of cartridge 17, clutch assembly 50 and drive mechanism 16 until the cartridge 18 and the clutch assembly 50 reach their respective proximal stop positions.

Preferably, proximal stop position of the cartridge 17 and proximal stop position of the clutch assembly 50 are correlated with respect to each other. The cartridge 17 is in its distal stop position when the cupped fixing sleeve 22 abuts with a proximal end face of the proximally inwardly directed shaft 40 of the cartridge holder section 12 of the housing. The clutch assembly 50, in particular its second clutch element 54 reaches its distal stop position, when the wedge-shaped and radially extending protrusion 62 of the second clutch element 54 props against the stop element 44, which, in the illustrated embodiment, coincides with the proximal end face of the cartridge holder section 12.

In an initial configuration of the drug delivery device 10 as illustrated in FIG. 14, the clutch assembly 50 is in a locking configuration. First and second clutch elements 52, 54 are separated by a gap 76 under the effect of the intermediary spring 56. As can be further seen in FIG. 15, the clutch assembly 50 is in its proximal stop position and the first clutch element 52 buts against a radially inwardly extending stop 80, which, in the present embodiment is integrally formed with the main housing section 14.

Starting from this initial configuration, a predefined dose to be injected can be selected, e.g. by dialling of the dose dial button 54. Consequently, the drive mechanism is displaced in proximal direction as illustrated in FIG. 16.

It is further to be pointed out, that in the initial configuration of FIG. 14 as well as after setting of a dose as illustrated in FIG. 16, the inner volume of the cartridge 17 is not yet in fluid transferring contact with the proximally inwardly pointing tipped end 29 of the injection needle 28.

A fluid-transferring coupling of injection needle 28 and cartridge 17 is achieved and conducted during a subsequent dose dispensing procedure. For this purpose, a user may exert distally directed thrust 96 to the dose button 100 as indicated in FIG. 17. Under the effect of the applied thrust 96, and due to the interlocking provided by the clutch assembly 50, the entire arrangement of cartridge 17, clutch assembly 50 and drive mechanism 16 is displaced in distal direction, because the piston rod 88 is hindered to rotatably move.

Consequently, cartridge 17, clutch assembly 50 and drive mechanism 16 are subject to a distally directed displacement until the cartridge 17 and/or the clutch assembly 50 reach their distal stop position. During this distally directed movement, the applied thrust 96 is almost exclusively transferred to the sidewall 18 of the cartridge 17 via the first clutch element 52 and by means of its axially extending strut sections 64.

As soon as the second clutch element 54 abuts against the proximal end face 44 of the cartridge holder section 12, as illustrated in FIG. 18, a further distally directed displacement of the piston rod 88 leads to a compression of the spring element 56. The two clutch elements 52 and 54 are brought together in axial direction such that a clamping of the two-fold threaded engagement of piston rod 88 and the two inner threads 59, 61 is effectively annulled. Hence, the clutch assembly 50 is switched into its release configuration.

Consequently, the piston rod 88 becomes free to rotate and hence to conduct a combined rotational and distally directed movement with respect to the sidewall or housing 18 of the cartridge 17. This way, the piston 20 can be driven in distal direction by a pre-defined distance governed by the size of the previously set dose.

In the illustrated embodiment, the two-fold threaded engagement of the piston rod 88 with respect to the drive sleeve 90 as well as with respect to the rotatably locked clutch assembly 50 provides a beneficial reduction gear mechanism with its gear ratio being governed by the ratio of the different leads at opposite end sections of the piston rod 88.

Even though the present invention is exemplary illustrated with only one representative drive mechanism 16, the releasable coupling of piercing element 28 and cartridge 17 as well as the axial displacement of the drive mechanism 16 and the cartridge 17 is generally not limited to a single drive mechanism. It may be universally applied to a variety of drive mechanisms, wherein a piston rod 88 is generally subject to an axial and/or rotational movement during dose dispensing.

After completion of dose injection, distally applied thrust 96 is typically reduced. As soon as the thrust 96 drops below a predefined threshold, the spring element 31 tends to displace the entire assembly of cartridge 17, clutch assembly 50 and drive mechanism 16 to their respective proximal stop positions, thereby disconnecting cartridge 17 and injection needle 28. At the same time, the spring element 56 of the clutch assembly 50 tends to axially separate first and second clutch elements 52, 54, such that the clutch 50 returns into its default interlocking configuration.

In such disconnected configuration droplet generation, which might be due to elastic relaxation of septum 24 and/or piston 20, can be effectively minimized or even entirely eliminated.

The invention claimed is:

1. Drug delivery device for dispensing of a dose of a medicinal product, comprising:
    a housing having a proximal main housing section and a distal cartridge holder section;
    a drive mechanism comprising an axially displaceable piston rod to act on a piston of a cartridge containing the medicinal product to be dispensed, wherein the cartridge holder section is threaded to support a piercing element which is threadedly connectable to the cartridge holder section and which is adapted to penetrate a distal end face of the cartridge,
    a biasing member operably engaged with the housing and with the cartridge, the biasing member configured to reversibly displace the cartridge proximally from a distal stop position to a proximal stop position in an axial direction and with respect to the cartridge holder section to disconnect the cartridge from the piercing element while the piercing element remains fastened to the cartridge holder section, wherein in the distal stop position the cartridge is connected to the piercing element and wherein in the proximal stop position the cartridge is disconnected from the piercing element such that a fluid transfer between an inside volume of the cartridge and the piercing element is interrupted.

2. The drug delivery device according to claim 1, wherein the cartridge is reversibly displaceably supported in the housing between the proximal and distal stop position.

3. The drug delivery device according to claim 1, wherein the cartridge is spring-supported in distal direction against a distal end section of the housing.

4. The drug delivery device according to claim 1, wherein the drive mechanism is adapted to selectively act on a proximal end section of the cartridge's sidewall and/or on a proximal end face of the piston.

5. The drug delivery device according to claim 1, wherein the piston rod is radially guided by a clutch assembly which is adapted to transfer a distally directed thrust either to the sidewall of the cartridge or to the piston.

6. The drug delivery device according to claim 5, wherein the clutch assembly is axially displaceably guided in the housing.

7. The drug delivery device according to claim 5, wherein the clutch assembly is secured against rotation with respect to the housing.

8. The drug delivery device according to claim 5, wherein in a locking configuration the clutch assembly substantially impedes a rotation of the piston rod.

9. The drug delivery device according to claim 5, wherein the clutch assembly in its release configuration allows for an axial movement of the piston rod with respect to the sidewall of the cartridge.

10. The drug delivery device according to claim 5, wherein the clutch assembly comprises a first and a second clutch element and an intermediary spring element adapted to axially separate first and second clutch elements.

11. The drug delivery device according to claim 10, wherein the piston rod is threadedly engaged with the first and with the second clutch element.

12. The drug delivery device according to claim 10, wherein the first clutch element comprises at least one axially extending strut section at least partially radially surrounding the second clutch element and being further adapted to be operably engaged with the sidewall of the cartridge.

13. The drug delivery device according to claim 10, wherein the second clutch element comprises at least one projection radially extending between adjacent strut sections of the first clutch element, wherein during displacement of the cartridge to its distal stop position, said projection axially abuts against a stop element of the housing such that first and second clutch elements are brought together against the action of the spring element for releasing of the clutch assembly.

14. The drug delivery device according to claim 1, wherein the main housing section is adapted to receive the drive mechanism and wherein the cartridge holder section is adapted to slidably receive the cartridge, wherein a proximal end section of the cartridge holder section is arranged in a distally located receptacle of the main housing section, such that a proximal end face of the cartridge holder section serves as an axial stop element.

15. The drug delivery device according to claim 1 further comprising a cartridge being at least partially filled with a medicinal product to be dispensed by the drug delivery device, the cartridge comprising:
 a sidewall of substantially tubular shape,
 a proximal end section having a cross-sectional diameter sealed by an axially displaceable piston, and
 a distal end section having a diameter and sealed by a seal having a section being penetrable by a piercing element, wherein the diameter of the distal end section or a surface of the pierceable section of the seal is smaller than 30% of the cross-sectional diameter of the proximal end section of the tubular sidewall.

16. A cartridge for a drug delivery device wherein said cartridge being at least partially filled with
 a medicinal product to be dispensed by the drug delivery device, where the drug delivery device has
 a housing having a proximal main housing section and a distal cartridge holder section;
 a drive mechanism comprising an axially displaceable piston rod, wherein the cartridge holder section is threaded to support a piercing element which is threadedly connectable to the cartridge holder section and which is adapted to penetrate a distal end face of the cartridge,
 a biasing member operably engaged with the housing and with the cartridge, the biasing member configured to reversibly displace the cartridge proximally from a distal stop position to a proximal stop position in an axial direction and with respect to the cartridge holder section to disconnect the cartridge from the piercing element while the piercing element remains fastened to the cartridge holder section, wherein in the distal stop position the cartridge is connected to the piercing element and wherein in the proximal stop position the cartridge is disconnected from the piercing element such that a fluid transfer between an inside volume of the cartridge and the piercing element is interrupted, and where the cartridge further comprises,
 a sidewall of substantially tubular shape,
 a proximal end section having a cross-sectional diameter sealed by an axially displaceable piston,
 a distal end section having a diameter and sealed by a seal having a section being penetrable by a piercing element, wherein the diameter of the distal end section or a surface of the pierceable section of the seal is smaller than 30% of the cross-sectional diameter of the proximal end section of the tubular sidewall.

17. The cartridge according to claim 16, wherein the diameter of the distal end section or a surface of the pierceable section of the seal is smaller than 20% of the cross sectional diameter of the proximal end section of the tubular sidewall.

18. The cartridge according to claim 16, wherein the diameter of the distal end section or a surface of the pierceable section of the seal is smaller than 10% of the cross sectional diameter of the proximal end section of the tubular sidewall.

19. The cartridge according to claim 16, wherein the diameter of the distal end section or a surface of the pierceable section of the seal is smaller than 5% of the cross sectional diameter of the proximal end section of the tubular sidewall.

20. The drug delivery device according to claim 1 further comprising a clutch assembly threadedly engaged with the piston rod.

* * * * *